United States Patent [19]

Ackley

[11] Patent Number: 5,894,801
[45] Date of Patent: Apr. 20, 1999

[54] METHODS AND SYSTEMS FOR SENSING AND RECTIFYING PELLET SHAPED ARTICLES FOR SUBSEQUENT PROCESSING

[75] Inventor: E. Michael Ackley, Harbor, N.J.

[73] Assignee: Ackleey Machine Corporation, Moorestown, N.J.

[21] Appl. No.: 08/941,399

[22] Filed: Sep. 30, 1997

[51] Int. Cl.⁶ .............................. B41F 13/24; B41F 17/08
[52] U.S. Cl. .......................... 101/485; 101/2; 101/40; 209/586; 209/587; 250/559.26; 356/237
[58] Field of Search ................... 101/2, 37, 38, 101/39, 40, 483, 485; 209/522, 558, 580, 581, 582, 586, 587; 250/559.26; 356/237

[56] References Cited

U.S. PATENT DOCUMENTS

| | | | |
|---|---|---|---|
| 3,123,217 | 3/1964 | McMillan et al. | 209/586 |
| 3,601,041 | 8/1971 | Perra, Jr. et al. | 101/37 |
| 3,618,764 | 11/1971 | Bawdualak . | |
| 3,670,865 | 6/1972 | Garland | 101/37 |
| 3,709,598 | 1/1973 | Vandenberg et al. | 209/587 |
| 4,082,188 | 4/1978 | Grimmell et al. . | |
| 4,143,770 | 3/1979 | Grimmell et al. . | |
| 4,189,996 | 2/1980 | Ackley, Sr. et al. | 101/37 |
| 4,208,962 | 6/1980 | Ackley, Sr. et al. | 101/40 |
| 4,254,704 | 3/1981 | Ackley, Sr. et al. | 101/37 |
| 4,266,477 | 5/1981 | Ackley . | |
| 4,266,478 | 5/1981 | Ackley | 101/40 |
| 4,335,810 | 6/1982 | Ackley et al. | 101/40 |
| 4,369,702 | 1/1983 | Ackley . | |
| 4,377,971 | 3/1983 | Ackley | 101/40 |
| 4,413,556 | 11/1983 | Ackley | 101/40 |
| 4,446,481 | 5/1984 | Edamatsu et al. | 250/559.26 |
| 4,500,012 | 2/1985 | Ackley . | |
| 4,991,223 | 2/1991 | Bradley . | |
| 5,021,645 | 6/1991 | Satula et al. . | |
| 5,087,965 | 2/1992 | Torre-Bueno . | |
| 5,376,771 | 12/1994 | Roy . | |
| 5,422,831 | 6/1995 | Misra et al. . | |
| 5,423,252 | 6/1995 | Yamamoto et al. | 101/40 |
| 5,463,465 | 10/1995 | Yamamoto et al. . | |
| 5,522,512 | 6/1996 | Archer et al. . | |
| 5,558,231 | 9/1996 | Weier . | |

*Primary Examiner*—Eugene H. Eickholt
*Attorney, Agent, or Firm*—Oliff & Berridge, PLC

[57] ABSTRACT

A dispenser dispenses pellet shaped articles onto a conveyer. The conveyer conveys the pellet shaped articles past a video sensor that senses any pellet shaped articles needing rotation so that they are uniformly oriented. The sensor provides a signal to a manipulating device which manipulates certain pellet shaped articles so that all of the articles are uniformly oriented. The conveyer transports the pellet shaped articles to a first pellet shaped article modifying device that, for example, prints indicia on the pellet shaped articles. A rectifying drum reorients all of the pellet shaped articles in order for printing to be performed on a reverse side. A second sensor and a second manipulating device may also be provided. An inspection system to determine whether a pellet shaped article is defective after a performed modification is also provided.

40 Claims, 13 Drawing Sheets

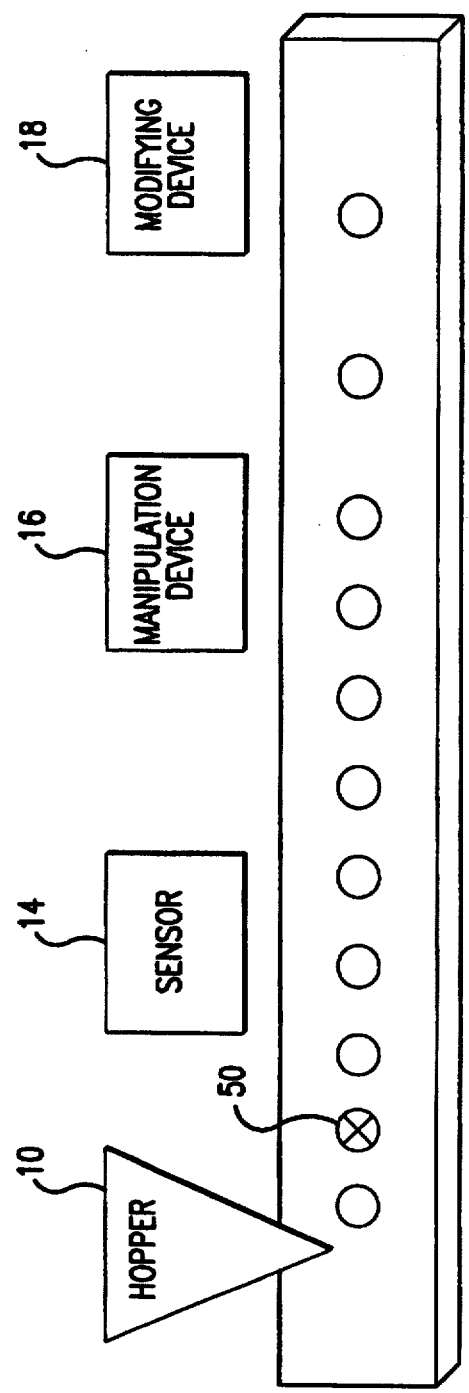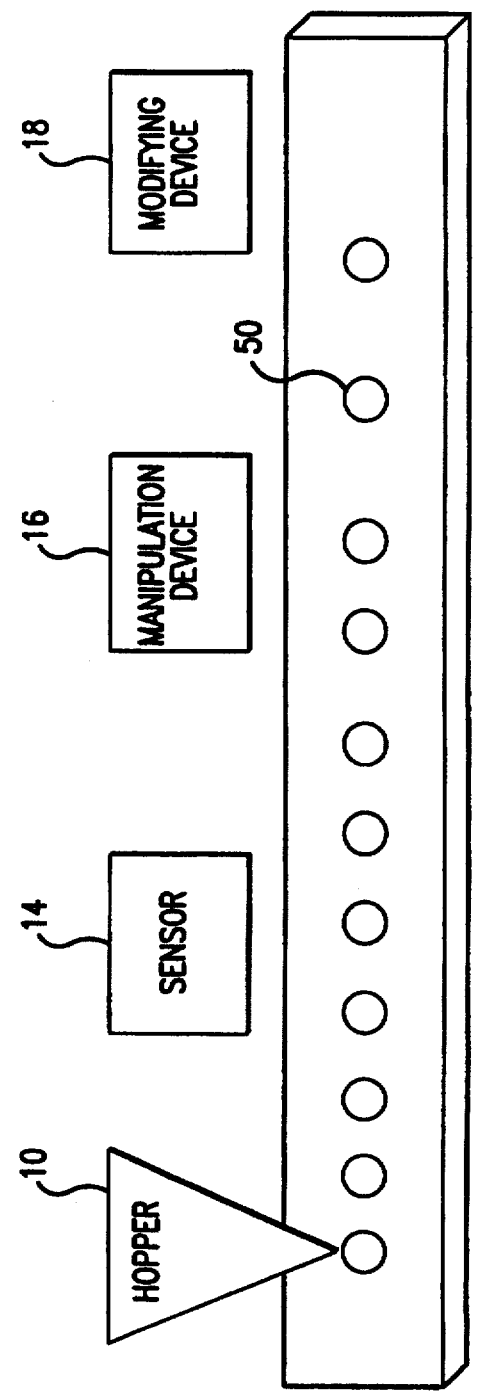

5,894,801

METHODS AND SYSTEMS FOR SENSING AND RECTIFYING PELLET SHAPED ARTICLES FOR SUBSEQUENT PROCESSING

BACKGROUND OF THE INVENTION

1. Field of the Invention

The invention relates generally to a method and system for sensing and rectifying pellet shaped articles for subsequent modification, processing, and/or inspection. In particular, the invention relates to a system that senses articles and rectifies them in a predetermined orientation for subsequent modification (e.g., printing). Following modification, the articles can be inspected for quality using an inspection system.

2. Background of the Invention

To ensure that a person is taking the proper dosage of medication, certain markings should be placed on the medication so that the person can be assured that he or she is taking the proper medications and in the proper dosages. In fact, the Food and Drug Administration requires certain markings for the safety of a consumer. These markings may include brand names, batch numbers, dosage amounts and the name of the manufacturer.

To print markings (e.g., indicia) on pellet shaped articles, many material orientation and printing devices have been devised. The printing devices include spin printers, laser printers and ink jet printers. One such example of material orientation and printing devices is disclosed in U.S. Pat. No. 4,369,702 to Ackley. This invention discloses an apparatus for processing, rectifying, orienting and imprinting indicia upon capsules that have dissimilar ends. In general, the invention includes three rotatable drums in tangential arrangement. Each drum is simultaneously rotated about an axis while transferring the capsules to each individual drum so as to properly orient them. After proper gravity orientation of the capsules, a spin printer prints indicia on the capsules.

It can also be desirable to print indicia on or modify both sides of the medication, whether it be capsules, tablets, pills or other types of medications. The foremost reason that printing indicia on both sides of the tablets is so important is for the safety of the consumer, e.g., when indicia is printed on both sides of tablets it is less likely that the consumer will consume the wrong medication. Additionally, when printing is performed on both sides of the tablets more information can be printed on the medication, e.g., the name of the manufacturer and the name of the medication. This will also assist the consumer in choosing the proper medication in the proper dosages. Of course, it may also be desirable to print indicia on or otherwise modify ends and/or edges of regularly or irregularly shaped pellet shaped articles.

There are known systems that print indicia on both sides of tablets. However, these systems are not designed to print indicia on tablets having different colored sides. In order to print indicia on tablets having different colored sides, a system must be able to sense that the proper colored side of the tablet faces each printer. This involves properly rectifying and orienting the tablets to ensure that the proper colored side of the tablet is being printed. It also involves having a proper printing indicia color to ensure that the printed indicia is visible.

To further complicate matters, it may be necessary to print indicia of different colors on different colored sides of the tablets. In these instances, it is not only necessary to rectify, orient and print on one side of the colored tablets, but for both sides. This involves first rectifying and orienting the tablets so that indicia can be properly printed on one side of all of the tablets and then repeating this process for the other (non-printed) side of the tablets. It is also imperative in this type of system to have printed indicia that is visible on both sides of the tablets. In systems in which printed matter matches the color of the reverse base color, it is particularly important to ensure that the proper side of the tablet receives the printed matter because the indicia would not be visible on the tablet due to insufficient contrast between the printed matter and the base color.

It is also very important for the manufacturer to carefully inspect the medication for defects, such as incorrect shape or printing, before the medication is distributed to the consumer. This is to ensure that the quality of the product is at the highest standards in order to protect the safety of the consumer. In most instances, current inspection systems allow many defective products to reach the consumer. Thus, a more reliable inspection system is needed to ensure the quality of the product and, in turn, to protect the safety of the consumer.

SUMMARY OF THE INVENTION

One aspect of the invention is directed towards a method and system for sensing and rectifying pellet shaped articles. Following rectification, the articles can be modified or processed in any desired fashion. For example, a printing device can print indicia, e.g. a logo, on the pellet shaped article. This allows, for example, the consumer to see what medication is being ingested prior to being consumed.

A dispenser is disposed over a conveyer and dispenses the pellet shaped articles onto the conveyer. The conveyer conveys the pellet shaped articles along a predefined path. Several dispensers well known in the art may be used by the present invention, including but not limited to, hoppers, rollers and feed dispensers.

The conveyer transports the pellet shaped articles past a sensor which senses the color, tone, shape or any other desirable characteristic (e.g., the presence of indicia) of the pellet shaped articles. The sensor senses which pellet shaped articles are to be rectified (e.g., flipped over or rotated) so that all of the pellet shaped articles face a same direction. The sensor provides a signal to a manipulation device that repositions, replaces, rotates or flips over certain pellet shaped articles.

After all of the pellet shaped articles are properly oriented, the articles can be modified or processed. For example, a pellet shaped article modifying device can include a printer, and further processing can include inspecting or packaging the articles.

The articles are oriented in the same direction (based on the sensor output) so that the same side of the articles receives the intended processing or modification. For example, multi-color articles often have indicia imprinted on one side of the articles representing, for example, the name of the medication, while the other side has the dosage information imprinted thereon. Thus, when printing on multi-colored articles, the contrast between the base color and the indicia must be sufficient for the printing to be effective. Moreover, the sensor may sense whether an article includes printing on one side such that the other side can be oriented to receive printing indicia or some other modification or processing. Additionally, the sensor may sense the shape of the article so that printing or other processing may be performed in a certain position in relation to the shape of the articles.

If desired, the conveyer transports the pellet shaped articles to a rectifying drum that rotates all of the articles so that printing can be performed on the reverse (non-printed) side of the pellet shaped articles.

The rectifying drum, however, may not properly orient all of the pellet shaped articles. If this occurs, a second sensor may be provided to sense any pellet shaped articles to be rotated or flipped over so that the non-printed side of the pellet shaped articles face a second printer.

Of course, the first and second modifying devices may be placed on opposite sides of the conveyor to substantially simultaneously perform the intended modifications after the articles are sensed and properly oriented.

Also, the first and second modifying devices may, for example, be drilling devices for drilling holes in the pellet shaped articles. This can provide a mechanical time release mechanism as disclosed in U.S. Pat. No. 5,376,771.

The present system also provides an inspection system for sensing the quality of the modified pellet shaped articles. In order to inspect the modified pellet-shaped articles, a rotating drum having a plurality of vacuum seats is provided. Additionally, a sensor that detects whether a pellet-shaped article is defective is also provided. If the sensor determines that a pellet-shaped article is defective, i.e., misshaped or misprinted, it provides a signal to a solenoid which controls the vacuum seats on the rotating drum. In embodiments, the defective articles may be received in the vacuum seats and the non-defective articles may be allowed to pass underneath the rotating drum. Alternatively, in embodiments, the defective articles may pass underneath the rotating drum and the non-defective articles may be received in the vacuum seats. In either case, the defective articles, may, for example, be discharged into a bin for future discarding, while the non-defective articles can be further processed or packaged.

These and other aspects and salient features of the invention will be described in or apparent from the following detailed description of preferred embodiments.

BRIEF DESCRIPTION OF THE DRAWINGS

Preferred embodiments of the invention will be described in conjunction with the following drawings, in which:

FIG. 7 shows a tablet having a side facing in a different direction than the remaining tablets;

FIG. 8 shows all of the tablets facing in the same direction;

DETAILED DESCRIPTION OF PREFERRED EMBODIMENTS

A method and system for sensing and rectifying pellet shaped articles is described. Preferably, the system rectifies pellet shaped articles so that printing indicia on tablets, pills, caplets and capsules (collectively known as "pellet shaped articles") in which each pellet shaped article has at least two colors and/or tones can be performed. Drilling and other modifications can also be performed using the video rectification system of the present invention. The dimensions of the invention, including length, width, shape, and other variables and quantities specified herein may vary with the type of system contemplated. Therefore, numbers and dimensions specified herein are not to be construed as limitations on the scope of the present invention. These numbers and dimensions are meant to be merely illustrative of one particular application.

Figure 1:
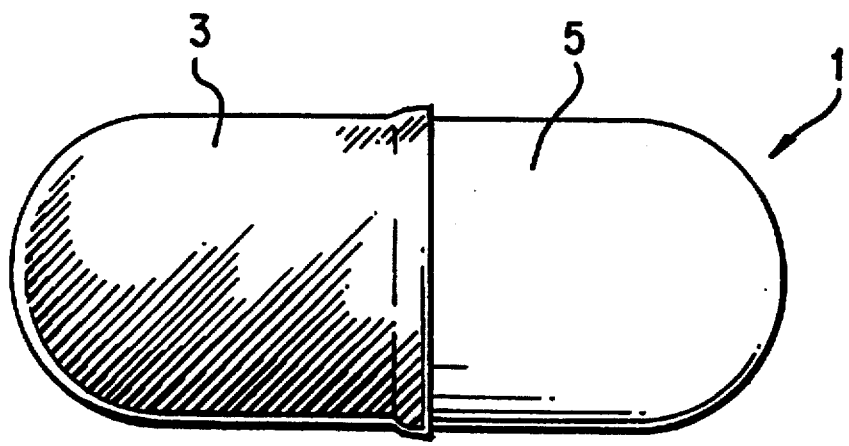
FIG. 1 shows an oval shaped capsule.

FIG. 1 shows an oval shaped capsule, generally depicted as 1. The oval shaped capsule 1 has a first side having a first color or tone 3 and a second side having a second color or tone 5. The capsule 1 can also be a "false" capsule in which a substantially solid tablet is formed in an oval shape (e.g., a caplet). The round shaped tablet 7 has a first side having a first color or tone 3 and a second side having a second color or tone 5. Various other shaped pellet shaped articles and coloring sequences, such as tones of various colors, are also contemplated for use in the present invention.

Figure 2:
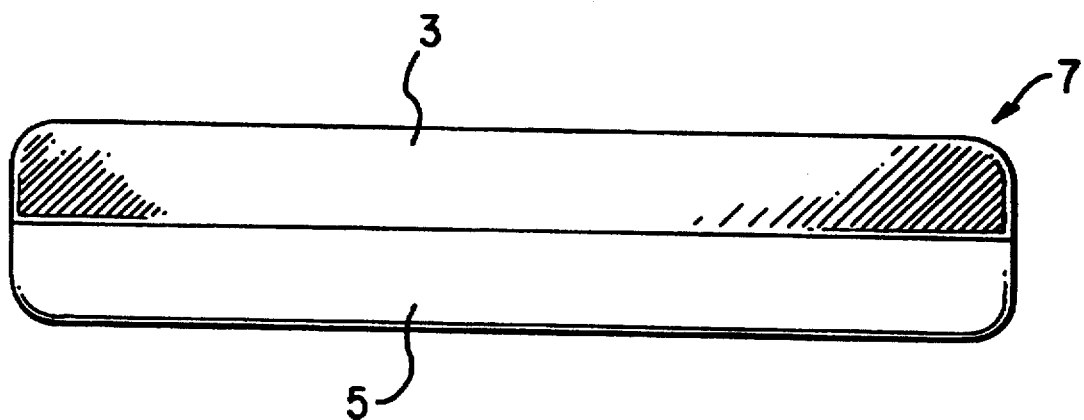
FIG. 2 shows a round shaped tablet.

For illustrative purposes only the first color or tone 3 of the oval capsule 1 and the first color or tone 3 of the round tablet 7 are the same color. Similarly, the second color or tone 5 of the oval capsule 1 and the second color or tone 5 of the round shaped tablet 7 are also the same color. Also for illustrative purposes, only the capsule and tablet shown in FIGS. 1 and 2, respectively, are described.

Figure 3:
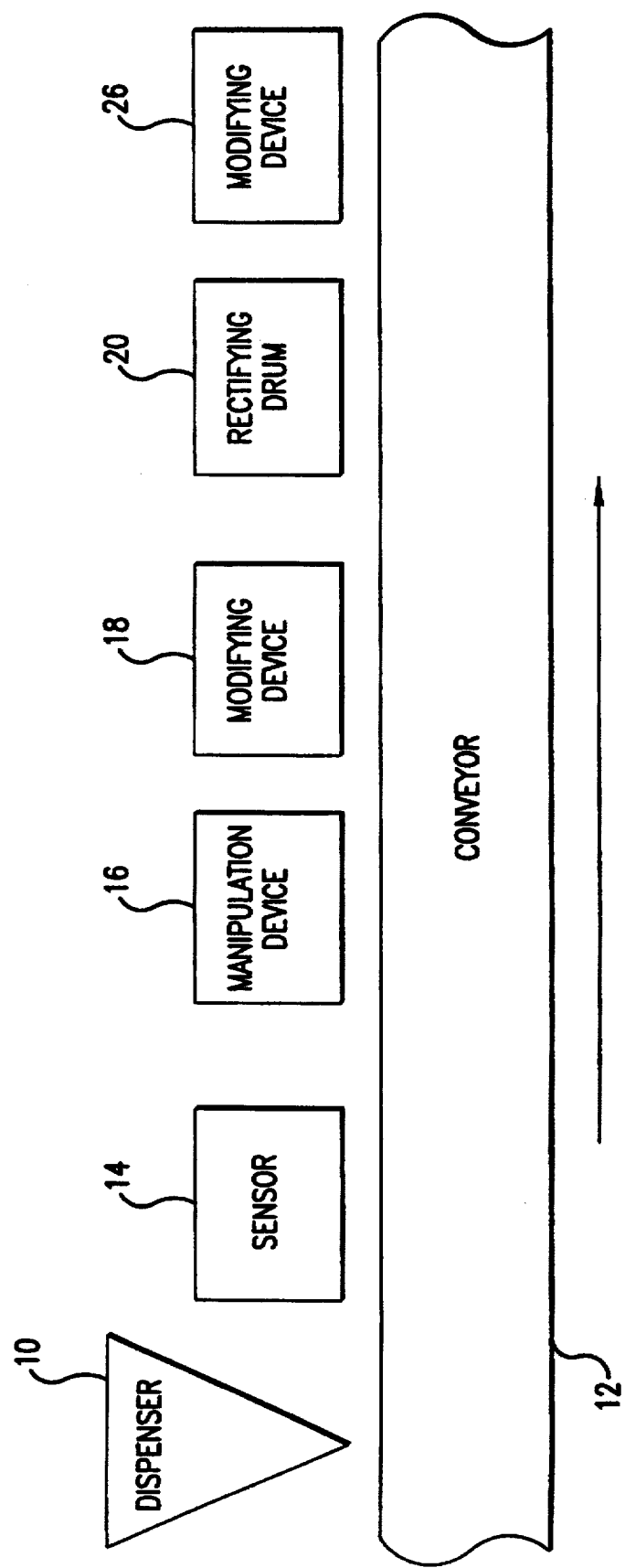
FIG. 3 shows an embodiment of the present invention.
Figure 4:
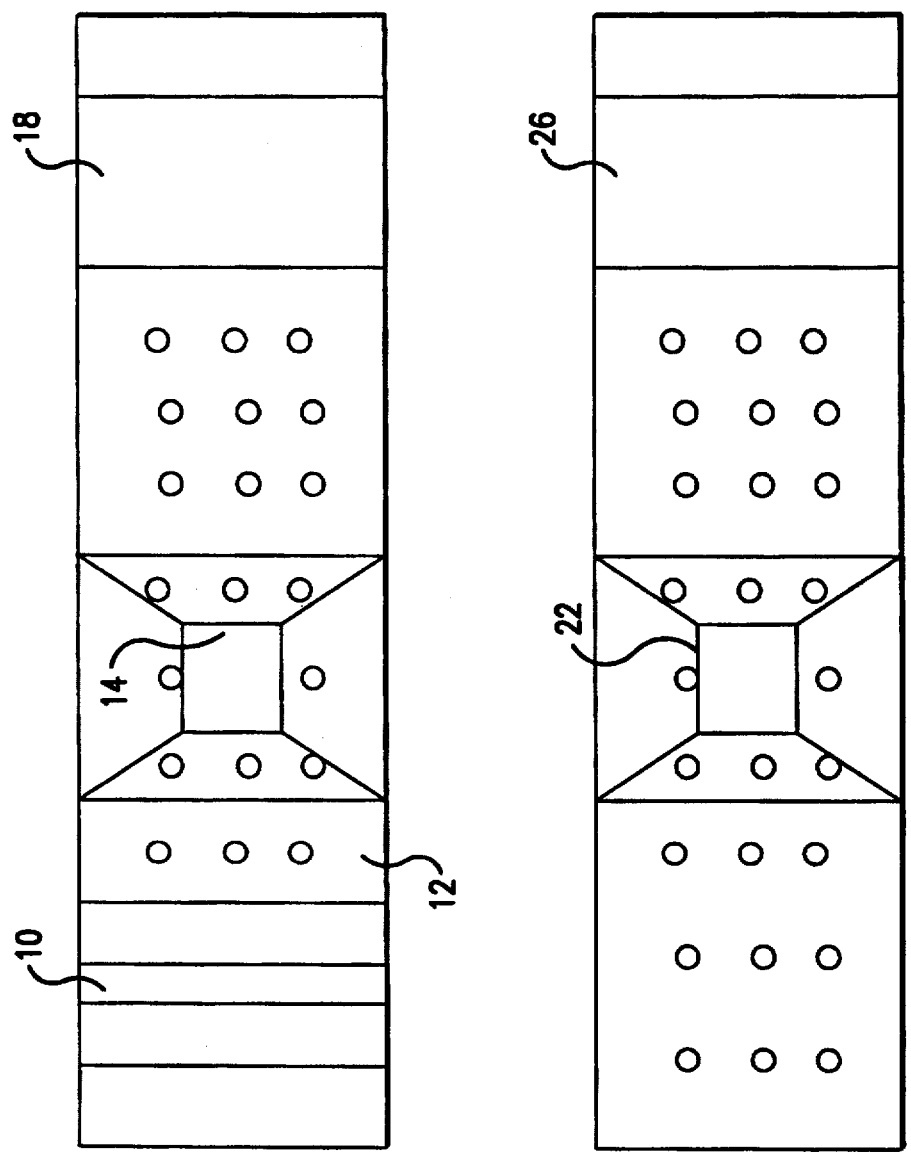
FIG. 4 shows a top view of a portion of a conveyer having several rows of two color tablets.
Figure 5:
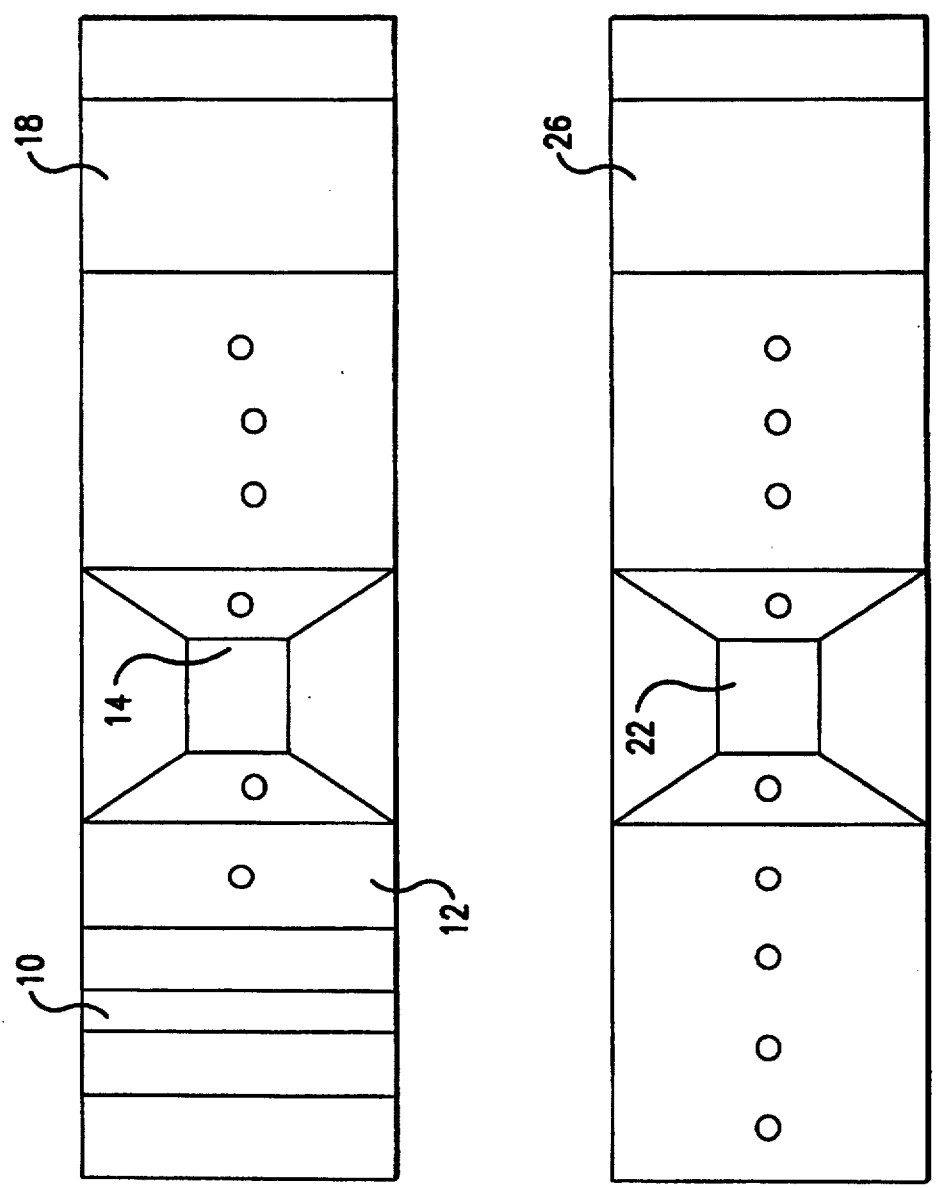
FIG. 5 shows a top view of a portion of a conveyer having one row of two color tablets.

FIG. 3 shows a first embodiment of the invention. A dispenser 10 (e.g., a hopper) is disposed over a conveyer 12 and dispenses pellet shaped articles onto the conveyer 12. The conveyer 12 conveys the pellet shaped articles along a predefined path. As seen in FIG. 4, the dispenser 10 can dispense several rows of pellet shaped articles onto the conveyer 12 simultaneously. Alternatively, as seen in FIG. 5, the dispenser 10 can dispense one row of pellet shaped articles onto the conveyer 12.

Several dispensers well known in the art may be used by the present invention, including but not limited to, hoppers, rollers and feed dispensers. In one preferred embodiment, a dispenser, such as disclosed in U.S. Pat. No. 4,500,012 to Ackley, incorporated herein by reference, is contemplated for use in the present invention.

The pellet shaped articles then pass a sensor 14, e.g., a video camera, that senses a predetermined characteristic of the articles. For example, the sensor 14 may be configured to sense a particular pattern or logo appearing on the articles, or the sensor may be calibrated to measure a certain wavelength of light. In this example, if the wavelength of light of a pellet shaped article does not fall within the calibrated wavelength range of the sensor 14, then those pellet shaped articles will be rectified (e.g., flipped over or rotated) or simply replaced in order to properly orient them for printing, drilling or other types of modifications. Alternatively, if the wavelength of light of the pellet shaped articles falls within the calibrated wavelength range of sensor 14, meaning that the articles are properly oriented, then those pellet shaped articles are not manipulated (replaced, rotated or flipped over), depending on the configuration of the present invention. If the sensor 14 is calibrated to sense only one color or tone of the pellet shaped articles, a sensor may be provided to determine whether the pellet shaped articles are actually seated on the conveyer 12.

In one preferred embodiment, the sensor 14 is calibrated to sense both the first color or tone 3 and the second color or tone 5 of the pellet shaped articles. In another embodiment, the sensor is calibrated to sense a shape of the article. For example, if the article is an irregular shape having, for example, irregular edges and/or sides, the sensor may sense one or more of the irregular sized edges and/or sides. The sensor 14 then senses which pellet shaped articles are to be manipulated, rotated or flipped over in order to properly orient all of the first color or tone 3 and all of the second color or tone 5 of the pellet shaped articles so that they face a common direction.

The sensor 14 may also sense the ends or sides of the pellet shaped articles. The first color or tone may appear on one end of an oblong capsule or caplet, or one side of a round tablet, while the second color or tone may appear on the other end of the capsule or caplet, or on the other side of the tablet. Alternatively, the sensor 14 may be calibrated to distinguish the larger side of a capsule. In an alternative embodiment, the sensor 14 may be calibrated to sense a printed or non-printed side of the pellet shaped articles, or any other predetermined or discernible characteristic of the articles, such as shape. The predetermined characteristic could include a sensed logo, color, or the positioning of the article with respect to the conveyor. For example, the sensor may ensure that the articles are placed on the conveyor in a predetermined position so that later modification or processing can be consistently performed.

The sensor 14 provides a signal to a manipulation device 16. The signal directs the manipulation device 16 to reposition, rotate, replace or flip over certain pellet shaped articles so that all of the first color or tone 3 and all of the second color or tone 5 of the pellet shaped articles face the same direction. Alternatively, the sensor 14 provides a signal to the manipulation device 16 so that the pellet shaped articles are rotated or flipped over according to the ends or sides of the pellet shaped articles. The articles may also be oriented so that a specific side of or edge of the articles focus a common direction. For example, if the articles are substantially tapered, the articles may be oriented so that the "point" of the article faces the same direction. When the pellet shaped articles pass the manipulation device 16, the manipulation device 16 rotates or flips over selected ones of the plurality of pellet shaped articles according to the signals provided by the sensor 14. The manipulation device 16 may be placed either on top of or underneath the conveyer 12 depending on the desired configuration.

In one preferred embodiment, the manipulation device 16 includes a plurality of concentrically placed drums (not shown), the pellet shaped articles which are misaligned (according to the sensor) are transferred from one rotating drum to another until they are properly oriented. See, e.g., U.S. Pat. No. 4,369,702, incorporated herein by reference. In yet another alternative, the manipulating device 16 may comprise a robotic arm (not shown) movable to manipulate the pellet shaped articles such that proper orientation is achieved. The robotic arm may be provided with a vacuum tip capable of holding the pellet shaped articles.

Once the manipulation device 16 repositions, rotates or flips over any misaligned pellet shaped articles so that all of the first color or tone 3 and all of the second color or tone 5 face in the same direction, i.e., all of the articles are properly oriented, the conveyer 12 transports the pellet shaped articles to a first pellet shaped article modifying device 18. Preferably, the first pellet shaped article modifying device 18 is a first printer, well known in the art.

If the first pellet shaped article modifying device 18 is a first printer, the first printer prints indicia on the pellet shaped articles. The first printer may be a laser printer, ink jet printer, spin printer or other well known printer capable of printing indicia on pellet shaped articles.

Preferably, the first printer prints indicia on the first color or tone 3 of all of the pellet shaped articles. The printing color should be sufficiently contrasted with the first color or tone 3. In one preferred embodiment, the printing color is substantially the same color as the second color or tone 5, i.e., the background or base color of one side or end of a pellet shaped article matches the indicia color for the other end or side of the pellet shaped article.

Alternatively, if the manipulation device 16 rotates or flips over the plurality of pellet shaped articles so that the second color or tone 5 faces the first printer, the first printer prints indicia on the second color or tone 5 of all of the pellet shaped articles. In this case, the printing color should be sufficiently contrasted with the second color or tone 5 and is preferably substantially the same color as the first color or tone 3, i.e., the background or base color of one side or end of the pellet shaped article matches the indicia color for the other end or side of the pellet shaped article. Other printing colors or tones are also contemplated for use with the printer.

In one preferred embodiment, the conveyer 12 transports the pellet shaped articles to a rectifying drum 20 which rotates or flips over all of the pellet shaped articles in order for a second pellet shaped modifying device 26 to modify the reverse side (e.g., non-printed) of the pellet shaped articles. Preferably, the second pellet shaped article modifying device 26 is a second printer for printing indicia on the non-printed side of the pellet shaped articles. Rectifying drums are well known in the art. One such rectifying drum is disclosed in U.S. Pat. No. 4,266,477 to Ackley, hereinafter incorporated by reference. Other rectifying drums are further contemplated for use in the present invention.

Referring again to FIG. 3, in embodiments, the rectifying drum 20, however, may not properly orient all of the pellet shaped articles. If this occurs, a second sensor 22 senses which pellet shaped articles are to be rotated or flipped over so that the reverse (non-printed) side of the pellet shaped articles faces the second pellet shaped article modifying device 26. Preferably, the second pellet shaped article modifying device 26 is the second printer. The second printer 26 may also be a laser printer, ink jet printer, spin printer or other well known printer capable of printing indicia on pellet shaped articles.

If the second pellet shaped article modifying device 26 is a second printer, the second sensor 22 provides a signal to a second manipulation device 24 to rotate or flip over the pellet shaped articles so that the second side or end of the pellet shaped articles faces the second printer. If printing was first performed on the second side or end of the pellet shaped articles, the second sensor 22 provides a signal to the second manipulation device 24 to rotate or flip over the pellet shaped articles so that the first side or end of the pellet shaped articles faces the second printer. Preferably, the indicia is a different color than the background or base color of one side or end on which printing is being performed. It is also preferred that the indicia substantially matches the base color of one side or end on which printing is not being performed. The second manipulation device 24 is similar to the manipulation device 16.

Figure 3A:
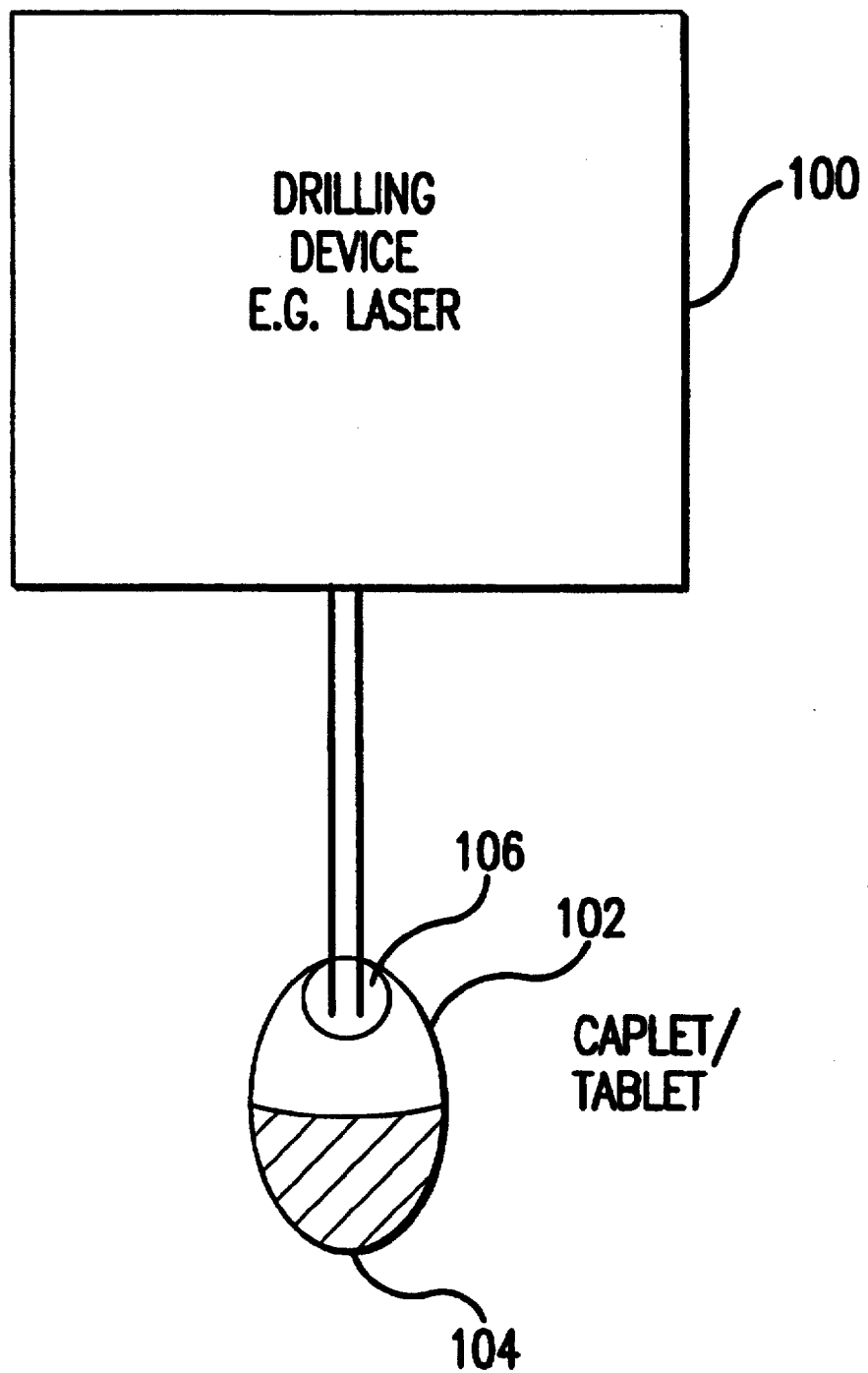
FIG. 3a shows a plan view of one embodiment of the pellet shaped article rectifying method and system for modifying pellet shaped articles according to the present invention using laser drilling.
Figure 3B:
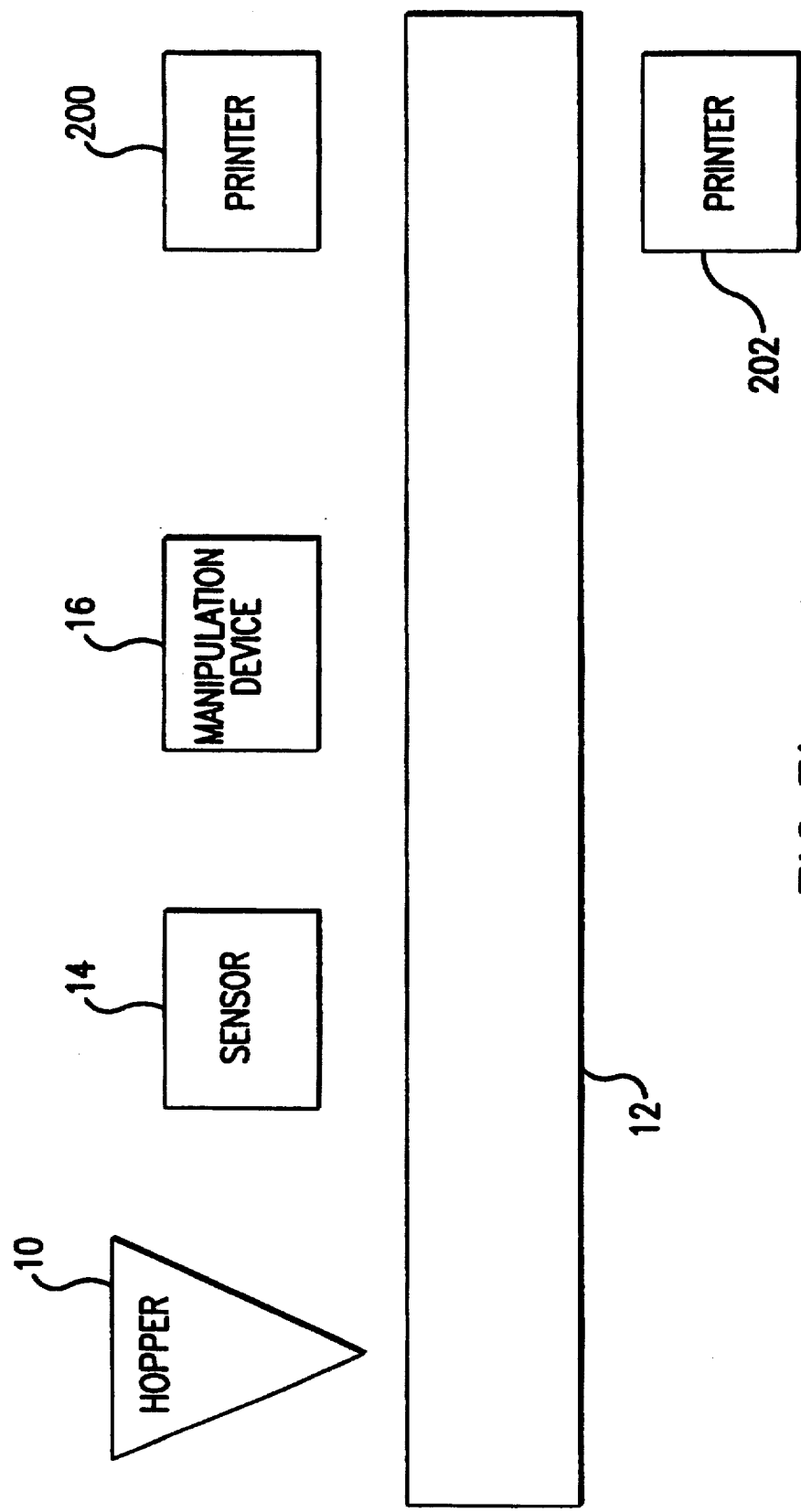
FIG. 3b shows an embodiment of the present invention.

Referring to FIG. 3b, in one preferred embodiment, printing is performed on both sides of the pellet shaped articles simultaneously. In order to print indicia on both sides of the pellet shaped articles simultaneously, a first printer 200 is placed on one side of the conveyer 12 and a second printer 202 is placed on the other side of the conveyer 12, opposite the first printer 200. The pellet shaped articles are dispensed from the dispenser 10 onto the conveyer 12 and the sensor 14 senses the sides, indicia characteristics, colors, shape or tones of the pellet shaped articles. The sensor 14 provides a signal to the manipulation device 16 to properly orient the pellet shaped articles prior to passing the first printer 200 and second printer 202 simultaneously. The manipulation device 16, in response to the signal, properly orients the pellet shaped articles so that printing can be performed. In one preferred embodiment, the first printer 200 prints a first indicia color on the first base color and the second printer 202 prints a second indicia color different than the first indicia color on the second base color of the pellet shaped articles. Preferably the first indicia color is substantially the same color as the second base color and the second indicia color is substantially the same color as the first base color. This process, for example, ensures that the printed indicia is visible on both sides and/or base colors of the pellet shaped articles when printing on both sides is performed simultaneously. U.S. Pat. No. 4,189,996, incorporated herein by reference, further describes simultaneously printing indicia on two sides of pellet shaped articles.

FIG. 3a also shows a laser 100 or other drilling device drilling a hole in a pellet shaped article having a first side 102 having a first base color and a second side 104 having a second base color. In this embodiment, the laser 100 drills a hole or a blind bore 106 into the first side 102. Depending on the orientation of the tablet or caplet, the laser 100 may also drill a hole 106 in the second side 104. The hole or blind bore provides a mechanical time-release mechanism. For example, the hole 106 exposes an active ingredient within the caplet or tablet. Once the caplet or tablet is ingested, the stomach acid and/or other intestinal secretions contact the active ingredient via the hole 106. This provides a mechanism in which the active ingredients (e.g. dosage) is delivered over a certain period of time. This, for example, allows the active ingredients of the caplet or tablet to be absorbed at different rates, as compared to a caplet or tablet that is not provided with a similar mechanical time-release mechanism. As a further example, U.S. Pat. No. 5,376,771, incorporated herein by reference, discloses a laser device for drilling holes in pharmaceuticals so that dosages can be varied over time.

FIG. 4 shows a top view of a portion of the conveyer 12 having several rows of two color pellet shaped articles. In FIG. 4, the dispenser 10 dispenses several rows of pellet shaped articles simultaneously. In this case the sensor 14 has a field of view of at least one column and all of the rows. When the dispenser 10 dispenses several rows of pellet shaped articles simultaneously, the first printer prints indicia on the pellet shaped articles simultaneously, as described above. The rectifying drum 20 rotates all of the pellet shaped articles so that all of the reverse (non-printed) sides of the pellet shaped articles face the second pellet shaped article modifying device 26 for modification. In alternate embodiments, if the rectifying drum 20 does not properly orient the pellet shaped articles, the second manipulation device 24 (not shown) may, for example, rotate or flip over those pellet shaped articles which were misaligned (e.g., improperly rotated or not rotated) by the rectifying drum 20 so that the reverse (non-printed) side of the pellet shaped articles (e.g., all of the same colors) faces the second pellet shaped article modifying device 26. The second pellet shaped article modifying device 26 prints indicia on the pellet shaped articles, as described above. The second pellet shaped article modifying device 26 may also drill holes in the pellet shaped articles or perform other modifications.

FIG. 5 shows a top view of a portion of the conveyer 12 having one row of pellet shaped articles. In FIG. 5, the dispenser 10 dispenses one row of pellet shaped articles at a time. In this case the sensor 14 also has a field of view of at least one column and one row of pellet shaped articles. The manipulation device 16 (not shown) rotates or flips over the one row of pellet shaped articles so that all of the first color or tone 3 and all of the second color or tone 5 face the same direction. The manipulation device 16 also rotates or flips over the pellet shaped articles according to the ends or sides of the pellet shaped articles. When the dispenser 10 dispenses one row of pellet shaped articles, the first pellet shaped article modifying device 18 prints indicia on one row of the pellet shaped articles at a time, as described above.

Referring again to FIG. 5, the rectifying drum 20 rotates all of the pellet shaped articles so that all of the reverse (non-printed) sides of the pellet shaped articles face the second pellet shaped article modifying device 26. The second sensor 22 also has a field of view of at least one column and one row of pellet shaped articles. In preferred embodiments, the second pellet shaped article modifying device 26 may be a printer so that indicia can be printed on the reverse side (e.g., non-printed side) of the pellet shaped articles.

In alternate embodiments, if the rectifying drum 20 does not properly orient the pellet shaped articles, the second manipulation device 24 (not shown) rotates those pellet shaped articles which are misaligned (e.g., improperly rotated or not rotated) by the rectifying drum 20 so that all of the same colors or tones of the reverse (non-printed) side of the pellet shaped articles are facing the second pellet shaped article modifying device 26. The second pellet shaped article modifying device 26 prints indicia on the pellet shaped articles, as described above. Alternatively, the second pellet shaped article modifying device may, for example, drill holes in the pellet shaped articles.

Figure 6:
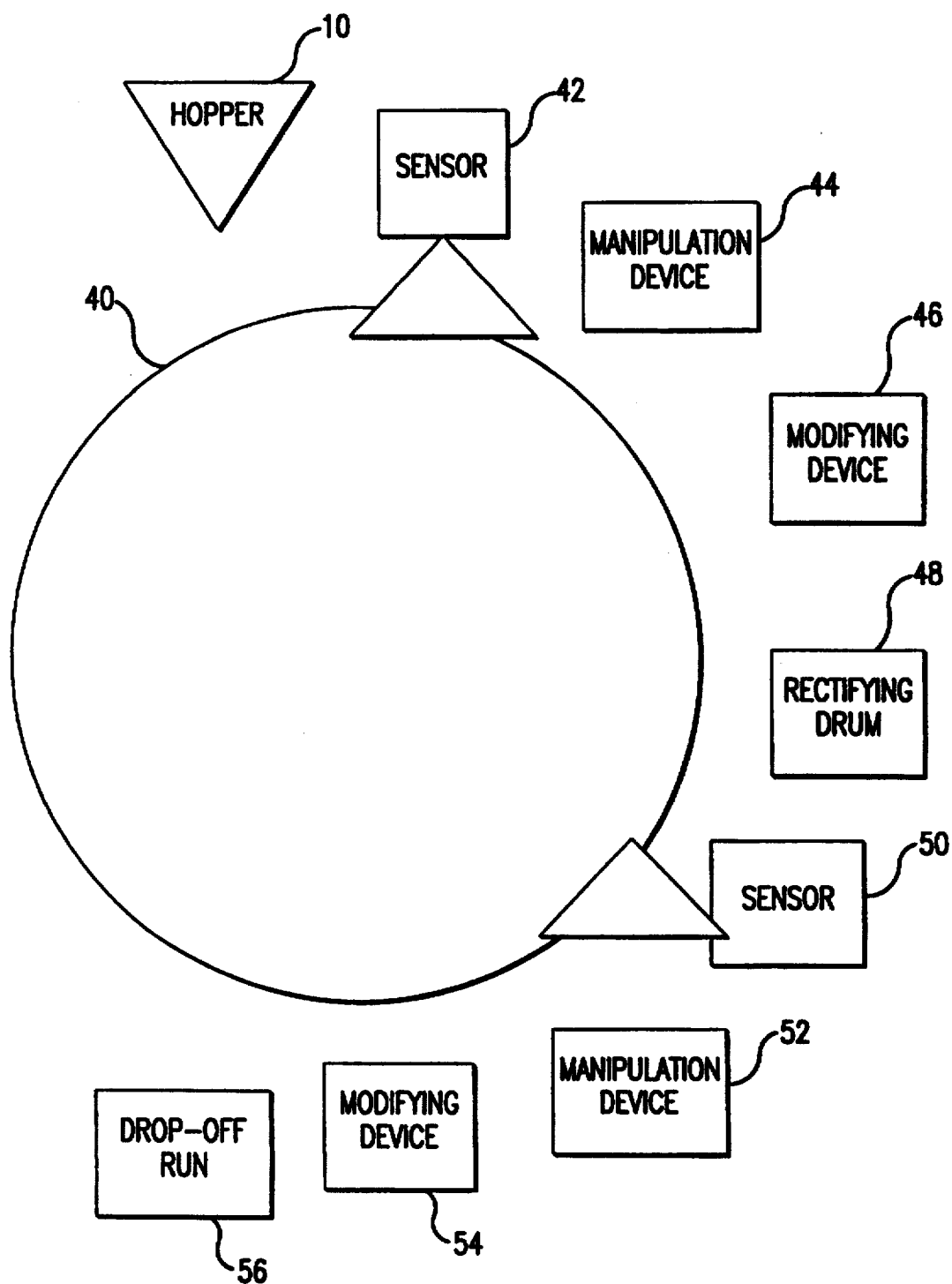
FIG. 6 shows a drum shaped conveyer.

FIG. 6 shows a drum-shaped conveyer 40. In this example, the pellet shaped articles are placed on the drum-shaped conveyer 40 by the dispenser 10. The pellet shaped articles are held in place by a vacuum or other similar mechanism. In one preferred embodiment, the drum-shaped conveyer 40 is also provided with a plurality of openings in which the pellet shaped articles are seated.

The drum-shaped conveyer 40 rotates the pellet shaped articles past a first sensor 42. The first sensor 42 senses which pellet shaped articles are to be rotated or flipped over in order to provide the proper orientation of the pellet shaped articles for printing, drilling or other modifications. In one preferred embodiment, the first sensor 42 senses the first color or tone 3 and the second color or tone 5. In this case, the first sensor 42 provides a signal to a first manipulation device 44 in order for all of the first color or tone 3 or all of the second color or tone 5 to face a first pellet shaped article modifying device 46, as described above. Alternatively, the first sensor 42 may sense a side or the shape of the article. In this case the first manipulation device 44 orients the articles so that printing can be uniformly accomplished on all of the articles.

The drum-shaped conveyer 40 then transports the pellet shaped articles to the first pellet shaped article modifying device 46. If the first pellet shaped article modifying device 46 is a first printer, the first printer 46 prints indicia on the pellet shaped articles. The indicia is substantially different from the color of the pellet shaped articles in which printing is being performed, as described above.

In one preferred embodiment, the drum-shaped conveyer 40 transports the pellet shaped articles to a rectifying drum 48. The rectifying drum 48 rotates or flips over all of the pellet shaped articles in order for a second pellet shaped article modifying device 54 to print indicia on the non-printed side of the pellet shaped articles, as described above.

In alternative embodiments, the rectifying drum 48 may not properly rotate or flip over all of the pellet shaped articles. If this occurs a second sensor 50 senses the printed side (or non-printed side or ends) of the pellet shaped articles. A signal is then provided to a second manipulation device 52 which rotates or flips over the pellet shaped articles so that the reverse (non-printed) side of the pellet shaped articles are all facing the second pellet shaped article modifying device 54. The second pellet shaped article modifying device 54 prints indicia on the non-printed side of the pellet shaped articles, as described above.

After completion of the printing, the drum-shaped conveyer 40 releases the pellet shaped articles into a drop off bin 56.

Printing on Tablets

One aspect of the present invention will now be described as it relates to rectifying and printing on substantially round-shaped tablets having different colored sides. This example is for illustrative purposes only.

FIGS. 7–10 show a tablet 50 dispensed from the dispenser 10 onto the conveyer 12. As seen in FIG. 7 the dispenser 10 may dispense the tablet 50 onto the conveyer so that a side (e.g. marked as "X") of the tablet 50 facing the first printer 18 is different than the sides of the remaining tablets facing the first printer 18. For clarity purposes only the "X" side of tablet 50 has a different characteristic, color or tone than the sides of the remaining tablets.

The conveyer 12 transports the tablets past the sensor 14. In one preferred embodiment, the sensor 14 senses the "X" side of tablet 50. The sensor 14 senses that the tablet 50 is to be rectified (e.g., flipped over or rotated) so that the "X" side of tablet 50 and the remaining tablet sides all face the same direction, i.e. towards the first printer 18.

The sensor 14 provides a signal to the manipulation device 16 which directs the manipulation device 16 to rotate or flip over the tablet 50 so that the "X" side of the tablet 50 faces the same direction as the remaining tablets on the conveyer 12 (e.g., the "X" side of the tablet 50 is now facing towards the conveyer 12). As seen in FIG. 8, when the tablet 50 passes the manipulation device 16, the manipulation device 16 rotates or flips over the tablet 50 according to the directions of the sensor 14.

Once the manipulation device 16 rotates or flips over the misaligned tablet 50, the conveyer 12 transports the tablets to the first printer 18. The first printer 18 prints indicia on all of the same sides of the tablets, as described above.

Figure 9:
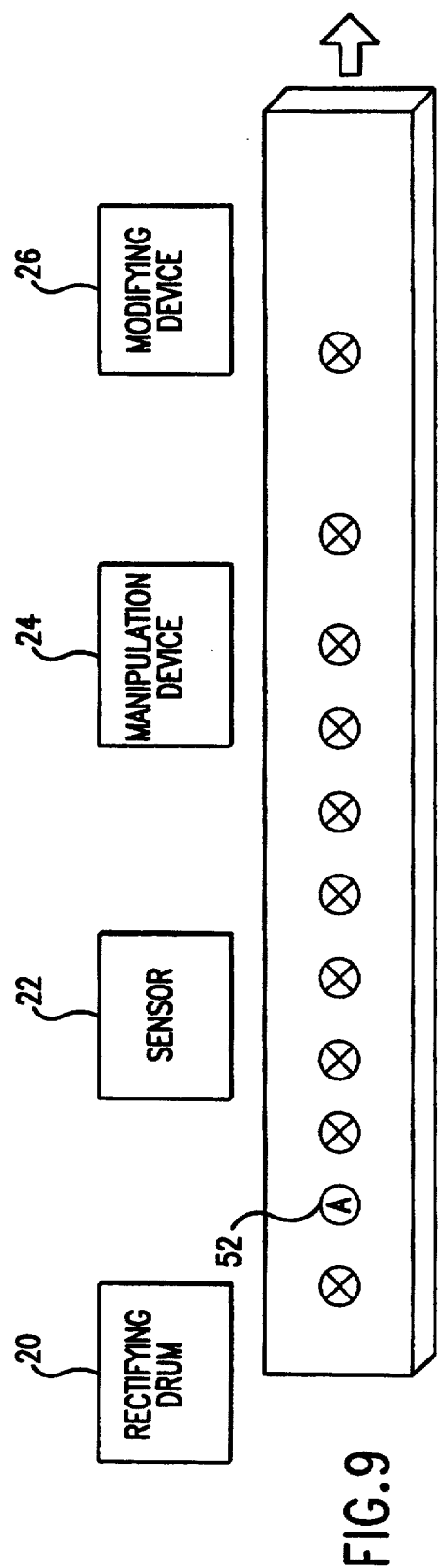
FIG. 9 shows a tablet having a side facing in a different direction than the remaining tablets.

In one preferred embodiment, the conveyer 12 transports the tablets to the rectifying drum 20. As seen in FIG. 9 the rectifying drum 20 rotates or flips over all of the tablets in order for drilling to be performed on the reverse (e.g., non-printed) side of the tablets. A second printer 26 then prints indicia on the non-printed side of the pellet shaped articles.

The rectifying drum 20, however, may not properly orient all of the tablets. As seen in FIG. 9, tablet 52 was not properly flipped over or rotated (e.g. an "A" side (depicting indicia) of tablet 52 faces the second printer 26).

Figure 10:
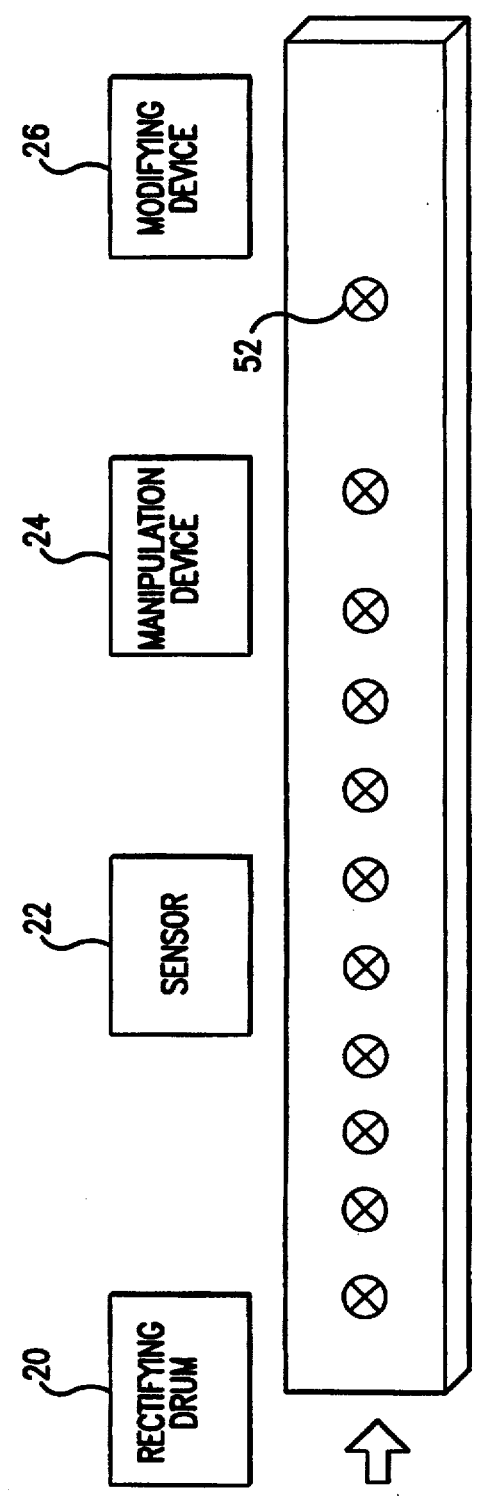
FIG. 10 shows all of the tablets facing in the same direction.

In one preferred embodiment the second sensor 22 senses the printed side (or characteristic, tone or color) of the tablet 52. Alternatively, the second sensor 22 senses the non-printed sides (or characteristic, tone or color) of the remaining tablets. The second sensor 22 provides a signal to the second manipulation device 24 which rotates or flips over the tablet 52 so that the reverse (non-printed) side (e.g., all of the same colors) is facing the second printer 26 (FIG. 10). The second printer 26 prints indicia on all of the tablets, as described above.

In another preferred embodiment, the same process and apparatus is used to drill holes into the sides or ends of the tablets, caplets and other pellet shaped articles.

Printing on Capsules

One aspect of the present invention will now be described as it relates to rectifying and printing indicia on capsules. This example is for illustrative purposes only.

Figure 11:
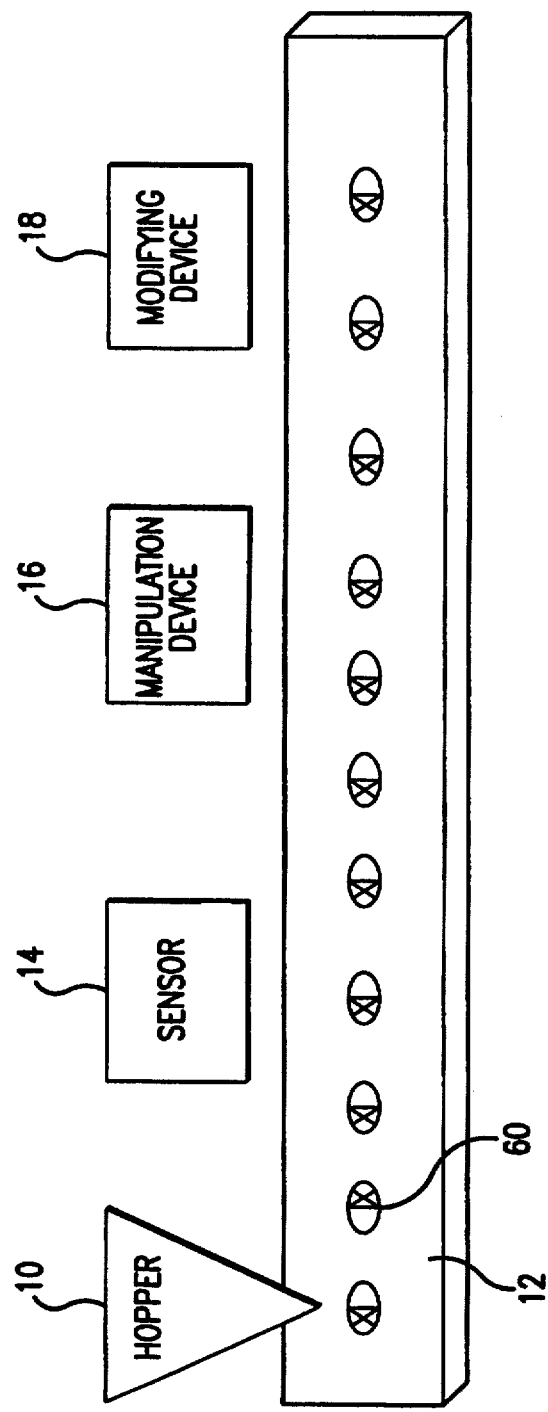
FIG. 11 shows a capsule with an end facing in a different direction than the remaining capsules.

FIGS. 11–14 show a capsule 60 dispensed from the dispenser 10 onto the conveyer 12. As seen in FIG. 11 the dispenser 10 may dispense a capsule 60 onto the conveyer so that an "X" side or end of the capsule 60 is facing a different direction than the "X" sides of the remaining capsules. For clarity purposes only the "X" side of capsule 60 has a different color, tone or cross sectional diameter than the other side of the capsules.

The conveyer 12 transports the capsule past the sensor 14. In one preferred embodiment, the sensor 14 senses the "X" side of capsule 60. Accordingly, the sensor may sense the tone, color or cross sectional diameter of the capsules. The sensor 14 senses that the capsule 60 is to be rectified (e.g., flipped over or rotated) so that the "X" side of capsule 60 faces the same direction as the "X" side of the remaining capsules, i.e., towards the first printer 18.

Figure 12:
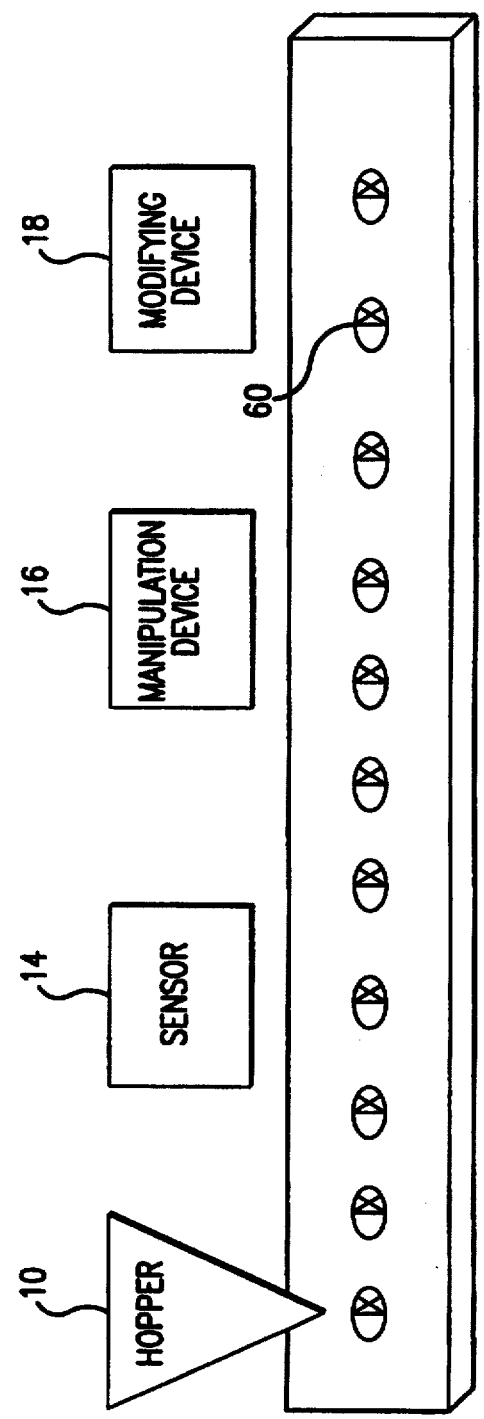
FIG. 12 shows all of the capsules facing in the same direction.

The sensor 14 then provides a signal to the manipulation device 16 which directs the manipulation device 16 to rotate or flip over the capsule 60 so that the "X" side of the capsule 60 faces the same direction as the "X" side of the remaining capsules (e.g., the "X" side of the capsule 60 is now facing towards the first printer 18). As seen in FIG. 12, when the capsule 60 passes the manipulation device 16, the manipulation device 16 rotates or flips over the capsule 60 according to the directions of the sensor 14.

Once the manipulation device 16 rotates or flips over the misaligned capsule 60, the conveyer 12 transports the capsules to the first printer 18. The first printer 18 prints indicia on all of the same sides of the capsules, as described above.

Figure 13:
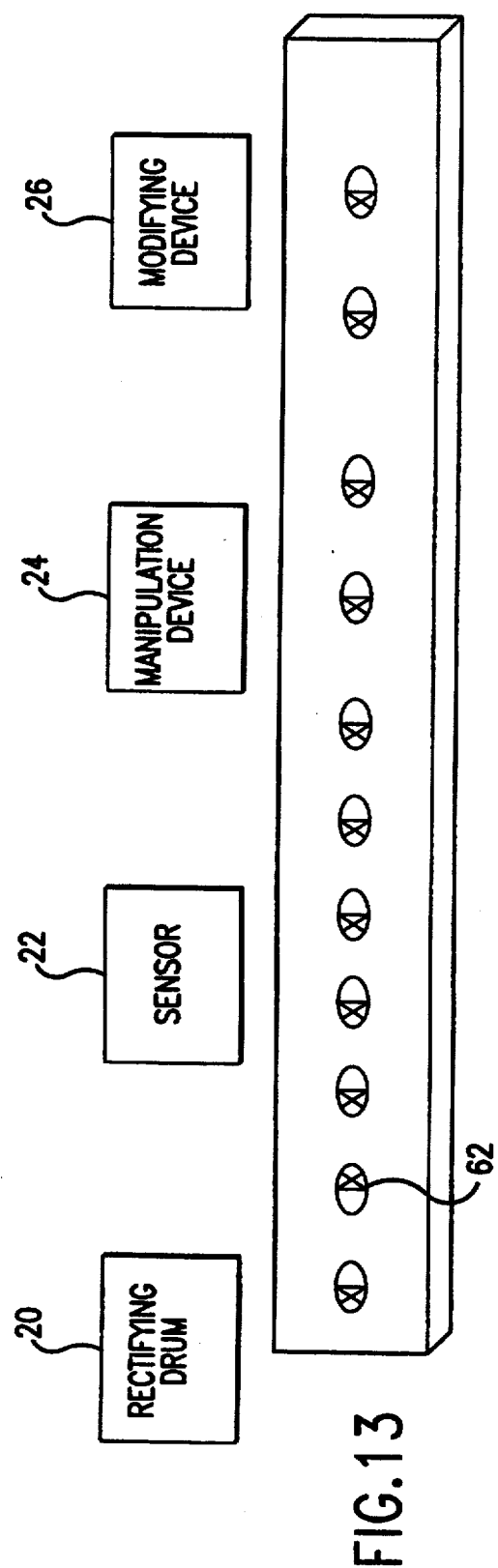
FIG. 13 shows a capsule with one end facing in a different direction than the remaining capsules.

In one preferred embodiment, the conveyer 12 transports the capsules to the rectifying drum 20. As seen in FIG. 13, the rectifying drum 20 rotates or flips over all of the capsules in order for indicia to be printed on the reverse (e.g., non-printed) side of the capsules.

The rectifying drum 20, however, may not properly orient all of the capsule. As seen in FIG. 13, capsule 62 was not properly flipped over or rotated (e.g. an "X"side of capsule 62 is facing the second printer 26).

Figure 14:
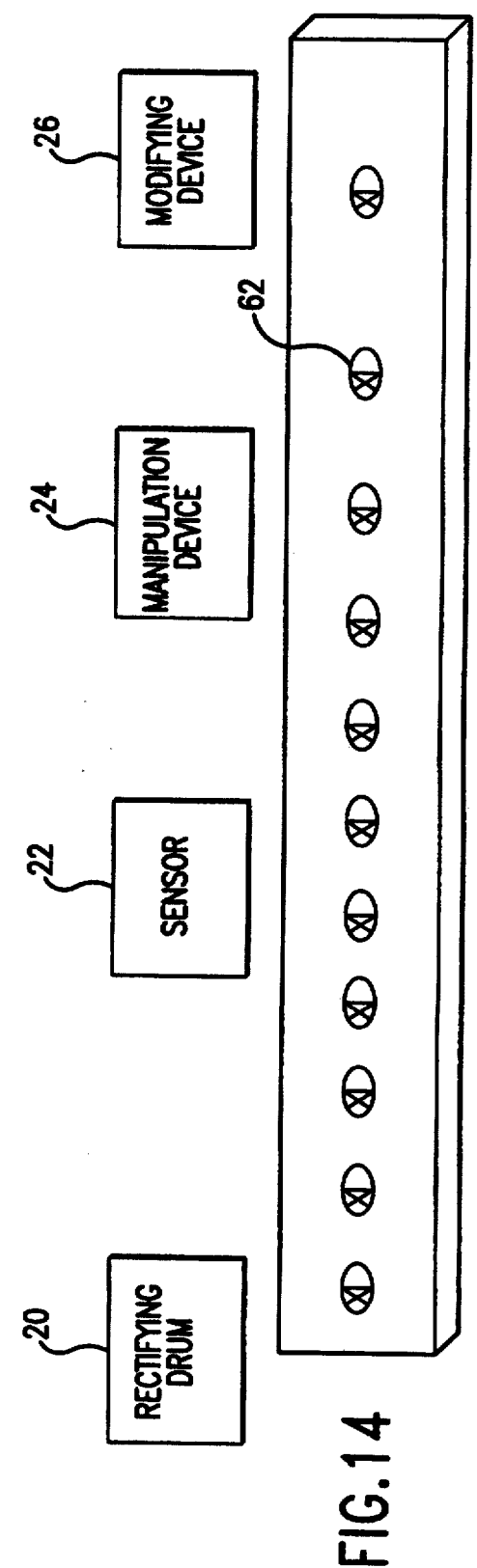
FIG. 14 shows all of the capsules facing in the same direction.

In one preferred embodiment, the second sensor 22 senses the printed side (tone, color or cross sectional diameter) of the capsule 62. Alternatively, the second sensor 22 senses the non-printed sides (or tone, color or cross sectional diameter) of the remaining capsules. The second sensor 22 provides a signal to the second manipulation device 24 which rotates or flips over the capsule 62 so that the "X" side (non-printed side) is facing the rectifying drum 20 and the non "X" side is facing the second printer 26 (FIG. 14). The second printer 26 prints indicia on all of the capsules, as described above.

Inspection of Pellet Shaped Articles

Figure 15:
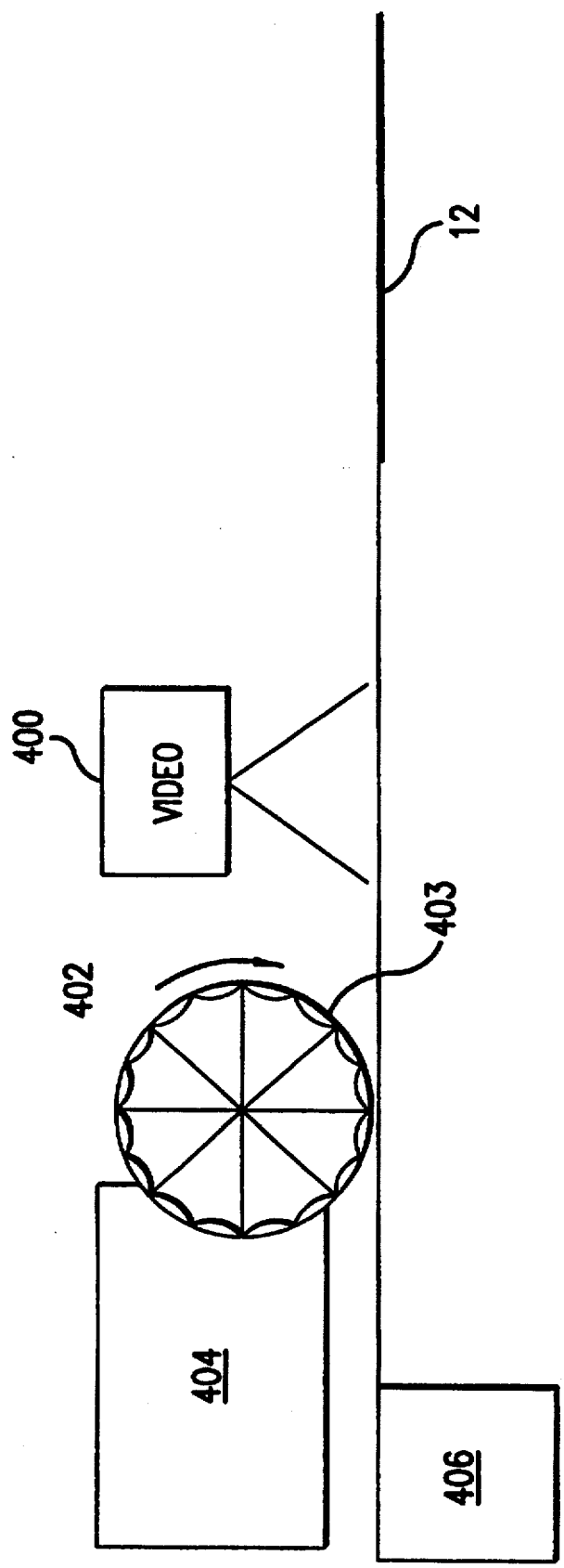
FIG. 15 shows another embodiment of the present invention.
Figure 16:
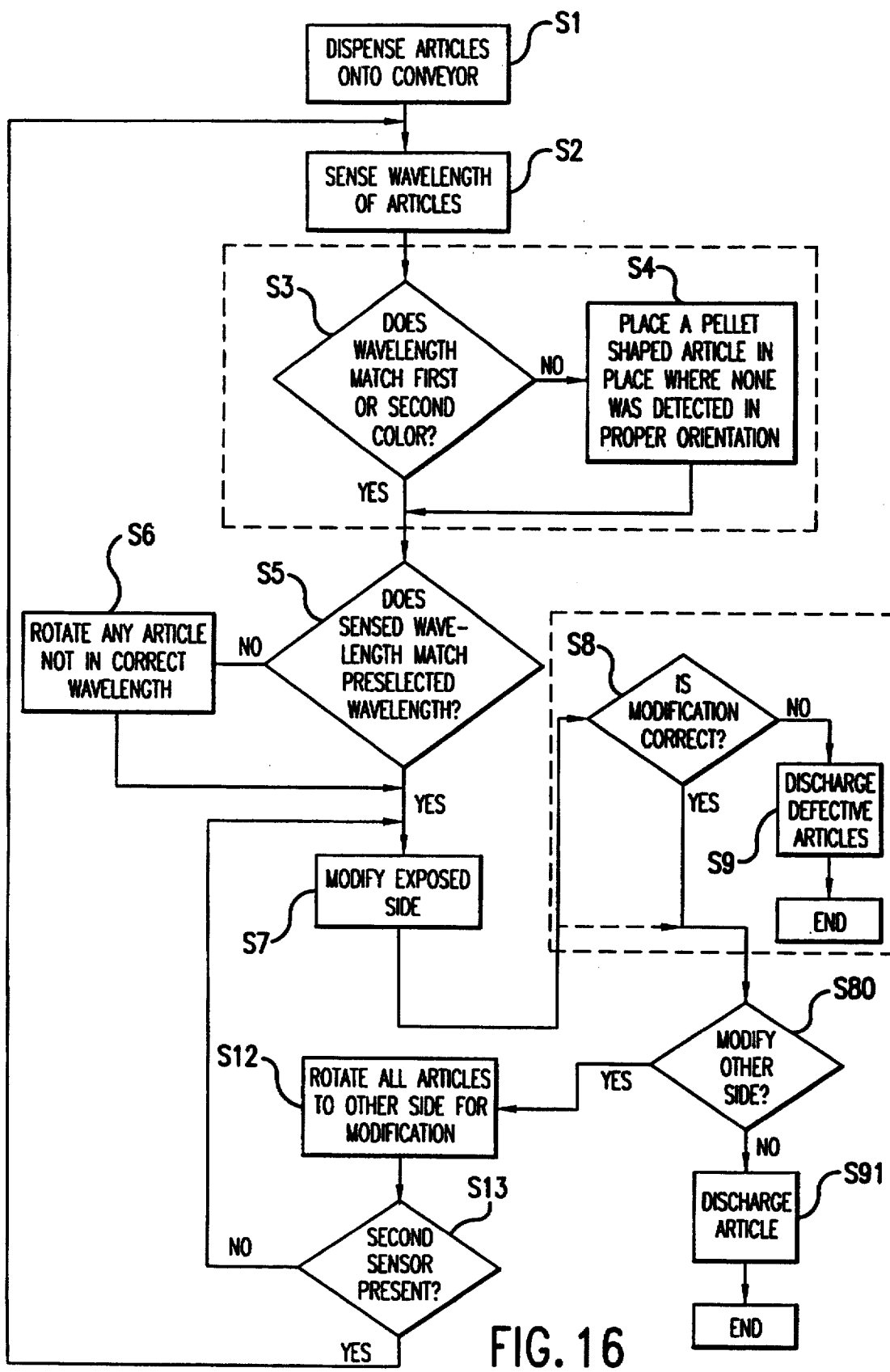
FIG. 16 shows an exemplary flowchart of one embodiment of the present invention.

Referring to FIG. 15, an inspection system is shown for sensing the quality of the articles after modification of the pellet shaped articles. A sensor 400 senses whether the pellet shaped articles are defective, e.g., not correctly modified such as, for example, misaligned printing or offset drilling. A rotating drum 402 having a plurality of vacuum seats 403 is synchronized with a movement of the conveyer 12 so that each one of the pellet shaped articles on the conveyer 12 substantially aligns with a corresponding vacuum seat 403. Each vacuum seat 403 is individually connected to a vacuum for providing a suctioning mechanism. The vacuum, in turn, for example, may be connected to a solenoid for controlling the suctioning of each vacuum seat 403, thus providing a mechanism to individually turn on and turn off each individual vacuum seat 403. If the sensor senses that any pellet shaped article is defective a signal is provided to the solenoid which, for example, turns off a particular vacuum seat 403 that aligns with the defective pellet shaped article. In this example, the defective pellet shaped article passes underneath the vacuum drum 402 without being "received", and is discharged into bin 406 for discarding. In alternate embodiments, the sensor 400 senses the shapes of the articles. If the shape of the article is defective, then a signal is provided to the solenoid which, for example, turns off a particular vacuum seat 403 so that the irregular shaped article can be discharged to bin 406 for discarding.

If the sensor 400 senses that the pellet shaped articles are correctly modified, e.g., not defective, then the vacuum seat 403 aligning with the non-defective pellet shaped article receives the non-defective pellet shaped article in the corresponding vacuum seat 403. The non-defective article is then discharged into bin 404 for future packaging, modification and/or consumer distribution.

The principles underlying the above-described inspection apparatus can also be applied to the manipulation devices 16 and 24 described above. For example, vacuum parts can be individually controlled to remove, replace or rotate misaligned pellet shaped articles.

Method of use

FIG. 15 is a flowchart of one preferred embodiment. At step S1 a dispenser dispenses the pellet shaped articles onto a conveyer. At step S2 a sensor senses a wavelength of the pellet shaped articles. Alternatively, the sensor may sense a side, end, color, shape or tone of the pellet shaped articles. For illustrative purposes only the sensor is calibrated to detect a certain wavelength of light.

At step S3 a determination as to whether the color of the first or second side of the pellet shaped article matches the wavelength range of the sensor is made. In one preferred embodiment, if the characteristic, color or tone of the pellet shaped articles is not detected, a dispensing mechanism can place a pellet shaped article on the conveyer at step S4 where no pellet shaped article was detected. Steps S3 and S4 are optional. If steps S3 and S4 are not present, the system may attempt to modify a pellet shaped article where none may be present if a pellet sensor per se is not provided.

At step S5 a sensor senses whether a wavelength of the pellet shaped article matches a preselected wavelength range of the sensor. The sensor can also determine whether another characteristic of the article is present, such as printing, a certain shape, etc. At step S6, if the wavelength of the pellet shaped article does not match the preselected wavelength range, it is manipulated (e.g., rotated flipped over or replaced) so that it matches the preselected wavelength range of the sensor. The pellet shaped article is then modified at step S7. Alternatively, if the wavelength of the pellet shaped article matches the preselected wavelength range in step S5 it is modified at S7 without performing step S6.

At step S8, a determination is made as to whether the pellet shaped article is defective, e.g., not correctly modified. If the pellet shaped article is defective it is discharged at step S9. If the pellet-shaped article is not defective a determination as to whether the non-modified side of the pellet shaped article is to be modified is performed at S10. Steps S8 and S9 are optional. If steps S8 and S9 are not present, then the system automatically goes to step S10. If no further modification is required, the pellet shaped article is discharged at step S11. If further modification is to be performed on the non-modified side of the pellet shaped article all of the articles are manipulated (e.g., rotated or flipped over) at step S12. At S13, if a second sensor is present, then the process is routed to step S2 so that the non-modified side can be modified in accordance with steps S2-S11. If a sensor is not present at step S13, modification of the pellet shaped articles is performed on the second exposed side at step S7, and are routed through steps S8-S11. As previously described, modification may include, for example, printing indicia on the pellet shaped articles and/or drilling holes in the pellet shaped articles.

Preferred and alternate embodiments of the invention have been described in detail. It is to be noted, however, that this description of these specific embodiments is merely illustrative of the principles underlying the inventive concept. It is therefore contemplated that various modifications of the disclosed embodiments will, without departing from the spirit and scope of the invention, be apparent to persons of ordinary skill in the art.

What is claimed is:

1. A pellet shaped article orienting apparatus, comprising:
   a conveyor that conveys a plurality of pellet shaped articles along a predefined path, the pellet shaped articles having at least a first side and a second side, at least one of the first and second sides including a predetermined characteristic;
   a dispenser that dispenses the pellet shaped articles on the conveyor;
   a sensor that senses the pellet shaped articles on the conveyor; and
   a manipulating device associated with the sensor that manipulates selected ones of the pellet shaped articles to uniformly orient all of the pellet shaped articles depending on whether a predetermined characteristic is detected by the sensor.

2. The apparatus of claim 1, wherein the sensor is a video camera.

3. The apparatus of claim 1, wherein the predetermined characteristic is at least one of printing indicia and a predetermined color.

4. The apparatus of claim 1, wherein the predetermined characteristic is a predetermined position of the articles with respect to the conveyor.

5. The apparatus of claim 1, further comprising a modifying device located downstream from the manipulating device that modifies at least one of the first and second sides of the pellet shaped articles.

6. The apparatus of claim 5 further comprising:

a rectifying device located downstream from the modifying device, the rectifying device rectifying all of the pellet shaped articles;

and a second modifying device that modifies the other of the first and second sides of the pellet shaped articles which are not modified.

7. A pellet shaped article rectifying and modifying apparatus, comprising:

a conveyer to convey a plurality of pellet shaped articles along a predefined path, the pellet shaped articles having a first side having a first base color and a second side having a second base color different from the first base color;

a pellet shaped article dispenser to dispense the pellet shaped articles onto the conveyer;

a pellet shaped article sensor located downstream of the pellet shaped article dispenser, the pellet shaped article sensor sensing at least one of the first and second base colors of the pellet shaped articles within a scanning area of the pellet shaped article sensor;

a manipulation device located downstream from the pellet shaped article sensor to manipulate selected ones of the pellet shaped articles in response to the base color detected by the pellet shaped article sensor so that all of the pellet shaped articles are uniformly oriented; and a pellet shaped article modifying device located downstream from the manipulation device for modifying the pellet shaped articles.

8. The apparatus of claim 7, wherein the pellet shaped article modifying device is a first printing device for printing indicia on the pellet shaped articles, the indicia being substantially different from one of the first base color and the second base color on which printing is performed.

9. The apparatus of claim 8, wherein the manipulation device selectively manipulates the pellet shaped articles so that one of the first base color and the second base color of the pellet shaped articles faces the first printing device.

10. The apparatus of claim 9, further comprising a second printing device aligned substantially with the first printing device, wherein the first and second printing devices substantially simultaneously print indicia on the first and second base colors of the pellet shaped articles.

11. The apparatus of claim 10, wherein the first printing device prints indicia on one of the first base color and the second base color, wherein the second printing device prints indicia on the other of the first base color and the second base color, wherein the indicia of the first printing device is different than the base color on which printing is performed with the first printing device, and wherein the indicia of the second printing device is different than the base color on which printing is performed with the second printing device.

12. The apparatus of claim 8, wherein the first printing device prints indicia on the first base color, and a printing color of the indicia substantially matches the second base color of the pellet shaped articles.

13. The apparatus of claim 8, further comprising:

a rectifying drum located downstream from the printing device to reorient all of the pellet shaped articles after the first printing device prints indicia on the pellet shaped articles; and a second printing device located downstream from the rectifying drum, the rectifying drum reorienting the pellet shaped articles so that a non-printed side of each of the pellet shaped articles faces the second printer, the second printing device printing indicia on the non-printed sides of the pellet shaped articles, the indicia of the second printing device being substantially different than the other of the first base color and the second base color of the non-printed sides.

14. The apparatus of claim 13, further comprising:

a second sensor located downstream from the rectifying drum for sensing at least one of the printed side and the non-printed side of the pellet shaped articles; and a second manipulation device located downstream from the second sensor to manipulate selected ones of the pellet shaped articles in response to signals of the second sensor.

15. The apparatus of claim 14, wherein the second manipulation device manipulates the pellet shaped articles so that the first base color faces the second printing device; and wherein the second printing device prints indicia on the first base color of the pellet shaped articles, the printing color of the indicia being substantially the same color as the second base color of the pellet shaped articles.

16. The apparatus of claim 14, wherein the second manipulation device manipulates selected ones of the pellet shaped articles so that the second base color faces the second printing device; and wherein the second printing device prints indicia on the second base color of the pellet shaped articles, the indicia being substantially the same color as the first base color of the pellet shaped articles.

17. The apparatus of claim 7, wherein the pellet shaped article modifying device is a drilling device for drilling holes in one of the first side and the second side of the pellet shaped articles.

18. The apparatus of claim 17, further comprising:

a rectifying drum located downstream from the drilling device to reorient all of the pellet shaped articles after the drilling device drills holes in the pellet shaped articles; and a second drilling device located downstream from the rectifying drum, the rectifying drum reorienting all of the pellet shaped articles so that a non-drilled side of each of the pellet shaped articles faces the second drilling device, the second drilling device drilling holes in the non-drilled sides of the pellet shaped articles.

19. The apparatus of claim 18, further comprising:

a second sensor located downstream from the rectifying drum for sensing at least one of the drilled side and the non-drilled side of the pellet shaped articles; and a second manipulation device located downstream from the second sensor to manipulate the pellet shaped articles, wherein the second manipulation device manipulates selected ones of the pellet shaped articles in response to the second sensor so that the non-drilled side faces the second drilling device, wherein the second drilling device drills holes in the non-drilled side of the pellet shaped articles.

20. The apparatus of claim 17, wherein the conveyer is a drum-shaped conveyor.

21. The apparatus of claim 20, wherein the drum shaped conveyor includes, in order, the sensor, the manipulation device, and the pellet shaped article modifying device.

22. The apparatus of claim 20, wherein the pellet shaped articles are held stationary in the drumshaped conveyer by vacuum means.

23. The apparatus of claim 7, wherein the pellet shaped article is a capsule having a first diameter end and a second diameter end smaller than the first diameter end, the sensor sensing one of the first diameter end and the second diameter end of the pellet shaped articles.

24. The apparatus of claim 23, wherein the first end has a first base color and a second end has a second base color.

25. A pellet shaped article rectifying and modifying apparatus, comprising:
- conveying means for conveying a plurality of pellet shaped articles along a predefined path, the pellet shaped articles having a first side having a first base color and a second side having a second base color;
- dispensing means for dispensing the pellet shaped articles onto the conveying means;
- sensing means for sensing at least one of the first and second base colors of the pellet shaped articles within a scanning area of the sensing means;
- manipulating means for manipulating selected ones of the pellet shaped articles in response to the base color detected by the sensing means so that all of the pellet shaped articles are uniformly oriented; and
- pellet shaped article modifying means for modifying the pellet shaped articles.

26. The apparatus of claim 25, wherein the pellet shaped article modifying means comprises printing means for printing indicia on the pellet shaped articles, the indicia being substantially different from one of the first base color and the second base color of the pellet shaped articles on which printing is performed.

27. The apparatus of claim 26, further comprising:
- rectifying means for manipulating all of the pellet shaped articles after the printing means prints indicia on the pellet shaped articles; and
- second printing means, the rectifying means manipulating the pellet shaped articles so that non-printed sides of the pellet shaped articles face the second printing means, the second printing means printing indicia on the non-printed sides of the pellet shaped articles, the indicia being substantially different than the other of the first base color and the second base color of the non-printed sides.

28. The apparatus of claim 27, further comprising:
- second sensing means for sensing one of the printed sides and non-printed sides of the pellet shaped articles; and
- second manipulation means for manipulating selected ones of the pellet shaped articles in response to the second sensing means.

29. The apparatus of claim 28,
- wherein the second manipulating means manipulates the pellet shaped articles so that the non-printed sides of the pellet shaped article face the second printing means; and
- wherein the second printing means prints indicia on the non-printed sides of the pellet shaped articles, the indicia being substantially different than the other of the first base color or the second base color of the non-printed sides.

30. The apparatus of claim 29, wherein each of the pellet shaped articles has a first end having a first cross-sectional diameter and a second end having a second cross-sectional diameter, the first cross-sectional diameter being different than the second cross-sectional diameter.

31. The apparatus of claim 30,
- wherein the sensing means senses one of the first cross sectional diameter and the second cross sectional diameter;
- wherein the rectifying means manipulates the pellet shaped articles in response to the sensing means; and
- wherein the printing means prints indicia on one of the first cross sectional diameter and the second cross sectional diameter, the indicia being substantially different than a base color on which printing is performed.

32. The apparatus of claim 31,
- wherein the second manipulation means manipulates the pellet shaped articles after the printing means prints indicia on the pellet shaped articles, and
- wherein the second printing means prints indicia on the non-printed sides of the pellet shaped articles, the indicia being substantially different than a base color of the non-printed side.

33. The apparatus of claim 25, wherein the pellet shaped article modifying means comprises drilling means for drilling holes in the pellet shaped articles.

34. The apparatus of claim 33, further comprising:
- rectifying means for reorienting all of the pellet shaped articles after the drilling means drills the pellet shaped articles; and
- second drilling means, the rectifying means manipulating the pellet shaped articles so that non-drilled sides of the pellet shaped articles face the second drilling means, the second drilling means drilling holes on the non-drilled sides of the pellet shaped articles.

35. The apparatus of claim 34, further comprising:
- second sensing means for sensing one of the drilled sides and non-drilled sides of the pellet shaped articles; and
- second manipulation means for manipulating selected ones of the pellet shaped articles in response to the second sensing means so that the second drilling means drills holes in one of the non-drilled side and drilled side of the pellet shaped articles.

36. A pellet shaped article inspection apparatus, comprising:
- a conveyor that conveys a plurality of pellet shaped articles along a predefined path;
- a pellet shaped article sensor located substantially adjacent to the conveyor, the pellet shaped article sensor being configured to determine whether any of the pellet shaped articles are defective;
- a vacuum drum positioned above the conveyor and being associated with the pellet shaped article sensor, the vacuum drum having a plurality of vacuum receiving holes each receiving one of the pellet shaped articles, the vacuum drum including a control device for selectively activating the vacuum receiving holes in response to the determination of the pellet-shaped article sensor, wherein defective articles are not received in the vacuum receiving holes of the vacuum drum.

37. The apparatus of claim 36, wherein non-defective pellet shaped articles are received in the vacuum receiving holes of the vacuum drum by selective activation of a vacuum and are ejected into a drop off bin.

38. A method of orienting pellet shaped articles, comprising:
- dispensing a plurality of pellet shaped articles on a conveyor;
- conveying the pellet shaped articles along a predefined path, the plurality of pellet shaped articles having at least first and second sides, one of said first and second sides including a predetermined characteristic;
- sensing the pellet shaped articles on the conveyor; and rectifying selected pellet shaped articles while on the conveyor depending on whether the predetermined characteristic is sensed so that the pellet shaped articles are uniformly oriented on the conveyor.

39. The method of claim 38, further comprising modifying the pellet shape articles.

40. An apparatus for orienting pellet shaped articles, comprising: means for dispensing a plurality of pellet shaped articles on a conveyor;

means for conveying the pellet articles along a predefined path, the plurality of pellet shaped articles having at least first and second sides, one of said first and second sides including a predetermined characteristic;

means for sensing the pellet shaped articles on the conveying means; and means for rectifying selected pellet shaped articles while on the conveying means depending on whether the predetermined characteristic is sensed so that the pellet shaped articles are uniformly oriented on the conveying means.

* * * * *